(12) United States Patent
Chow et al.

(10) Patent No.: US 8,956,594 B2
(45) Date of Patent: Feb. 17, 2015

(54) FLUORIDE-CALCIUM COMPOSITIONS, DENTAL PRODUCTS, AND METHODS FOR PROVIDING DENTAL FLUORIDE

(75) Inventors: Laurence C. Chow, Potomac, MD (US); Shozo Takagi, Gaithersburg, MD (US)

(73) Assignee: ADA Foundation, Chicago, IL (US)

(*) Notice: Subject to any disclaimer, the term of this patent is extended or adjusted under 35 U.S.C. 154(b) by 1929 days.

(21) Appl. No.: 11/552,414

(22) Filed: Oct. 24, 2006

(65) Prior Publication Data
US 2007/0098652 A1    May 3, 2007

Related U.S. Application Data

(60) Provisional application No. 60/730,761, filed on Oct. 27, 2005.

(51) Int. Cl.
| | | |
|---|---|---|
| *A61K 8/21* | (2006.01) | |
| *A61K 8/24* | (2006.01) | |
| *A61K 33/06* | (2006.01) | |
| *A61Q 11/00* | (2006.01) | |
| *A61K 8/19* | (2006.01) | |

(52) U.S. Cl.
CPC . *A61Q 11/00* (2013.01); *A61K 8/19* (2013.01); *A61K 8/21* (2013.01); *A61K 8/24* (2013.01)
USPC ............... 424/52; 424/49; 424/57; 424/401; 424/602; 424/682

(58) Field of Classification Search
USPC ........ 424/52, 49, 57, 401, 602, 682; 433/215, 433/216, 217.1
See application file for complete search history.

(56) References Cited

U.S. PATENT DOCUMENTS

| | | | |
|---|---|---|---|
| 3,670,076 A |  | 6/1972 | Muhler |
| 3,765,577 A | * | 10/1973 | Burns, Jr. .................. 222/501 |
| 4,183,915 A | * | 1/1980 | Gaffar et al. .................. 424/52 |
| 4,420,312 A |  | 12/1983 | Wason |
| 4,532,124 A | * | 7/1985 | Pearce ........................ 424/52 |
| 5,476,647 A |  | 12/1995 | Chow et al. |
| 5,891,448 A |  | 4/1999 | Chow et al. |
| 2003/0003061 A1 |  | 1/2003 | Yue et al. |
| 2003/0152525 A1 |  | 8/2003 | Dixon |
| 2005/0037948 A1 |  | 2/2005 | Reynolds |
| 2005/0118115 A1 |  | 6/2005 | Fontenot |
| 2006/0171904 A1 |  | 8/2006 | Vogel et al. |
| 2008/0107611 A1 | * | 5/2008 | Sancho Riera et al. ......... 424/52 |

FOREIGN PATENT DOCUMENTS

ES    2226592    *    3/2005

OTHER PUBLICATIONS

Chow, L. and Takagi, S., "Deposition of Fluoride on Tooth Surfaces by a Two-Solution Mouthrinse In Vitro," Caries Res. 25:397-401 (1991).
Vogel, G. et al., "In Vivo Fluoride Concentrations Measured for Two Hours After a NaF or a New Two-Solution Rinse," J. Dent. Res. 71:448-452 (1992).
Vogel, G. et al., "Calcium Greatly Increases Salivary Fluoride from Fluoride Dentifrices/Rinses (abstract 3268)," J. Dent. Res. (Spec Iss. A) 84 (2005).
Takagi S. et al., "Effect of a Low-Fluoride-Content, Two-Component Rinse on Fluoride Uptake and on De- and Remineralization of Enamel Lesions: An In Vitro Study," Caries Res. 35:223-228 (2001).
Cherng et al., "Reduction in Dentin Permeability Using a Slurry Containing Dicalcium Phosphate and Calcium Hydroxide," J. Biomed. Mater. Red. Part B: Appl. Biomater. 78B:291-295 (2006).
Caries Research 2001;35:223-228; Effect of a Low-Fluoride-Content, Two-Component Rinse on Fluoride Uptade and on De- and remineralization of Enamel Lesions: An in vitro Study by: S. Takagi, H. Liao, L. C., Chow.
Research Reports, Clinical—Oct. 29, 1999; Remineralization Effects of a Two-solution Fluoride Mouthrinse: An in situ Study by: L.C. Chow, S. Takagi, C.M. Carey, and B.A. Sieck.
Caries Res 2002; 36:136-141, Remineralization Effect of a Low-Concentration Fluoride Rinse in an Intraoral Model, L.C. Chgow, S. Takagi, S. Frukhtbeyn, B.A. Sieck, E.E. Parry, N.S. Liao, G.E. Schumacher, M. Markovich.
Supplementary European Search Report EP 06836523.8, dated Jun. 28, 2011.
Extended European Search Report EP 06836523.8, dated Jun. 9, 2011.

* cited by examiner

*Primary Examiner* — Lezah Roberts
(74) *Attorney, Agent, or Firm* — Banner & Witcoff, Ltd.

(57) ABSTRACT

Disclosed are dental compositions and methods. In accordance with one embodiment, a dental composition includes calcium, fluorine, which is generally present in the form of fluoride, and phosphate or another stabilizing anion. The composition is stable as against precipitation of calcium fluoride during transport and storage, but is unstable against the precipitation of calcium fluoride in the oral cavity of a human. In many embodiments, the amount of fluoride may be less than the amount of fluoride used in a comparable composition intended for a similar purpose. A dental method comprises applying the composition to the oral cavity of a patient, whereupon calcium fluoride precipitates from the composition.

45 Claims, 4 Drawing Sheets

FLUORIDE-CALCIUM COMPOSITIONS, DENTAL PRODUCTS, AND METHODS FOR PROVIDING DENTAL FLUORIDE

CROSS REFERENCE TO RELATED APPLICATION

This application claims priority to prior U.S. provisional application Ser. No. 60/730,761, filed Oct. 27, 2005 the contents of which are incorporated by reference in their entireties.

STATEMENT OF FEDERALLY SPONSORED RESEARCH

The invention was made in the course of research supported at least in part by Grant DE05354 from the National Institute of Dental and Craniofacial Research and carried out at the National Institute of Standards and Technology. The U.S. government may have certain rights to the invention.

TECHNICAL FIELD

This invention is in the field of dental caries prevention, and specifically to compositions and products that contain fluorine for the provision of dental fluoride to a patient.

BACKGROUND OF THE INVENTION

It is well known in the art that dental fluoride is effective in impeding dental caries. Conventionally, dental fluoride is widely used in compositions in the form of rinses, toothpastes, and the like. Fluoride-containing mouth rinses that are formulated for daily use by consumers typically contain between 250 to 1,000 parts per million (ppm) fluoride, which ordinarily is present as sodium or stannous fluoride. Fluoride dentifrices typically contain 1,000 ppm to 5,000 ppm fluoride, which typically is present as sodium fluoride or sodium monofluorophosphate. Additionally, the prior art has provided self-applied fluoride gels, which typically have a fluoride content of up to 5,000 ppm. Office-administered topical fluoride gels, such as acidulated phosphate fluoride (APF) typically contain about 12,000 ppm (1.2%) fluoride.

The cariostatic effects of the various heretofore described fluoride regimens are believed to derive from their ability to deposit fluoride in plaque and salvia and onto the surfaces of teeth and other tissues in the mouth. Although the deposited fluoride is labile and leached out with time, daily applications of fluoride, such as via rinses and toothpastes, can maintain an elevated level of fluoride in the mouth. Additionally, the occasional application of gels, whether self-applied or office-administered, can further assist in maintaining an elevated content of fluoride on the surfaces of teeth.

Calcium fluoride, for $CaF_2$, is recognized in the art as being a significant labile oral fluoride reservoir. Numerous efforts have been made to provide compositions that allow for introduction of calcium fluoride to oral cavities. For instance, in Chow, L. and Takagi, S., "Deposition of Fluoride on Tooth Surfaces by a Two-Solution Mouthrinse In Vitro," *Caries Res.* 25:397-401 (1991), the inventors of the present application report that a rinse that contains both soluble calcium and fluoride did not increase fluoride deposition, because $CaF_2$ formed by rapid precipitation from a highly supersaturated solution was unable to be retained in a model substrate in vitro. Calcium fluoride may be introduced in a sustained precipitation process where hexafluorosilicate is a source of fluoride. See Vogel, G. et al., "In Vivo Fluoride Concentrations Measured for Two Hours After a NaF or a New Two-Solution Rinse," *J. Dent. Res.* 71:448-452 (1992). Similarly, enhanced fluoride deposition can be obtained from other systems; see, e.g., U.S. Pat. No. 5,476,647 (describing a complexed calcium source); U.S. Pat. No. 5,891,448 (describing a calcium fluoride inhibitor, such as citrate). In another approach, a calcium rinse is administered first, allowing calcium ions to penetrate into the surfaces of an oral substrate. Subsequently, fluoride is administered, causing $CaF_2$ to form within the surfaces of the oral substrates. Vogel, G. et al., "Calcium Greatly Increases Salivary Fluoride from Fluoride Dentifrices/Rinses (abstract 3268)," *J. Dent. Res.* (Spec Iss. A) 84 (2005).

Some of the prior art formulations are not stable for storage and transport, and typically, these formulations require that two components be provided. The two components must be combined and then used immediately. Additionally, certain prior art formulations are limited in the amount of fluoride that can be administered. For instance, certain compositions appear to be functional only when the fluoride concentration is no higher than 250 ppm for rinses, and no higher than 1,000 ppm for dentifrices.

The invention seeks, in certain embodiments, to provide a single composition that is stable for storage and transport as against precipitation of a fluoride containing material but that allows a fluoride containing material to precipitate in a human oral cavity. In some embodiments, the invention seeks to provide compositions that allow for greater deposition of fluoride than that permitted in the heretofore described products.

SUMMARY OF THE INVENTION

The invention provides, in its various embodiments, kits, methods, and compositions. In accordance with certain embodiments, a dental composition includes calcium, fluoride, and an acid or its anion, such as phosphoric acid or phosphate. The composition is sufficiently stable to inhibit precipitation of calcium fluoride during storage and transport of the composition, but is sufficiently unstable in a human oral cavity to cause precipitation of calcium fluoride. The composition may take any dentally suitable form, including toothpaste, gel, rinse, dentifrice, or the like. A method for providing dental fluoride may comprise providing such a composition and administering the composition to a patient. In some cases, the composition is self administered (particularly in the case of a toothpaste or rinse). A kit may include a sealed container that includes an amount of the composition sufficient to administer to at least one human, optionally in conjunction with tools for assisting in such administration (for instance, a dental tray or the like).

It has been observed in connection with many embodiments of the invention that the amount of calcium fluoride deposition that is produced using a composition of the invention is greater than that produced from a similar composition with the same amount of fluoride but not including the calcium or acid or anion. Thus, in some embodiments the amount of fluoride in a composition may be relatively reduced to yield a comparable amount of calcium fluoride deposition. This may be advantageous in certain embodiments, such as children's toothpastes.

Other features and embodiments are provided hereinbelow.

DETAILED DESCRIPTION OF CERTAIN EMBODIMENTS

Figure 1:
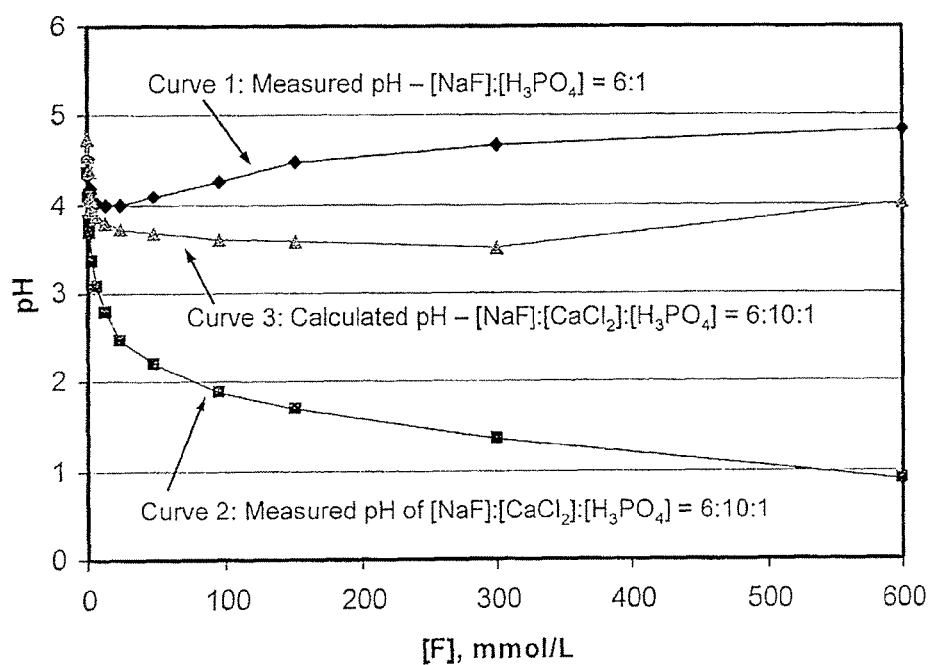
FIG. 1 is a graph that illustrates calculated and measured pH values as a function of fluoride concentration for certain compositions that contain sodium fluoride and phosphoric acid.

Generally, the invention contemplates a mixture that includes calcium, fluorine (generally as fluoride ion), and an acid or its anion in a biocompatible, dentally acceptable composition. In many embodiments, the calcium, fluoride, and acid or anion are present in an aqueous solution prior to introduction in vivo. The fluoride may be present as free fluoride free ion, or may be present in the composition in a different form. Likewise, the calcium and the acid or anion may be present in free ionic form or in different forms. It is contemplated in many cases that some portion of each of the components of the mixture will be present as free ions in solution, and another portion of each of the components will not be present as free ions.

The anion may be any suitable stabilizing anion, by which is contemplated to be an anion the inclusion of which results in a composition that is stable for storage and transport as against precipitation of calcium fluoride, the composition not being stable (or as stable) for storage and transport as against precipitation of calcium fluoride in the absence of the anion. In some embodiments, the anion contains the O—PO—O moiety. Phosphate, the anion of phosphoric acid, is believed to be suitable as an anion, as is glycerophosphate and possibly the anion of phosphonoacetic acid. In some trials, pyrophosphate, used in the absence of phosphate, was found not to be effective (although it is contemplated that this anion could be found suitable in other trials or in combination with other anions, and thus the claims are not intended to exclude this anion). It is believed that other anions may be found to be suitable for use in connection with the invention, in one or more embodiments. Plural anions may be employed in a single composition.

Some embodiments of the invention employ calcium, fluoride, and phosphate. The calcium, fluoride, and phosphate may be provided from any suitable materials, such as calcium chloride ($CaCl_2$), sodium fluoride (NaF), and phosphoric acid ($H_3PO_4$). Other suitable sources of calcium include calcium nitrate, calcium lactate, calcium glycerophosphate, calcium gluconate, calcium acetate, and calcium butyrate, and mixtures thereof. Other suitable sources of fluoride include potassium fluoride, stannous fluoride, ammonium fluoride, hydrogen fluoride, monofluorophosphate and hexafluorophosphate, and mixtures thereof. Other suitable sources of phosphate may include sodium, potassium, and ammonium phosphate, and mixtures thereof. More generally, other biocompatible sources of fluoride, phosphate, and calcium may be provided. Mixtures of any of the foregoing, in any suitable relative amounts, may be employed.

The compositions are stable for storage and transport, but are unstable in a human oral cavity, as against precipitation of calcium fluoride. Any suitable criterion for determining stability may be employed in analyzing a composition in accordance with one or more embodiments of the invention. For instance, in connection with one method for determining stability, a composition may be subjected to an artificial aging test, wherein a sample of the composition is stored at 50° C. at ambient pressure in a sealed container for 1 week. If calcium fluoride has not precipitated, or has precipitated in amounts that nonetheless render the compositions still usable in vivo, under this test the composition is deemed suitably stable for storage and transport. It is contemplated that other methods for determining and evaluating stability may be employed.

The composition may include fluoride, calcium, and phosphate (or other anion) in any suitable amounts and ratios useful for providing a composition that is stable for storage and transport but that is not stable as against calcium fluoride precipitation in a human oral cavity. In some embodiments, the ratio of fluoride to calcium is at most 2:1 (i.e., [F] divided by [Ca] or mol F/mol Ca is at most 2/1) (this and the following ratios being expressed on a molar basis). In other embodiments, the ratio of fluoride to calcium is at most 6:5. In some embodiments, the range of fluoride to calcium may range from 6:10 to 6:5. The amount of calcium may be increase relative to the amount of fluoride, and accordingly the F:Ca ratio can be less than 6:10; for instance, it can be 6:15, 6:20, 6:30, 6:40, or 6:50, or a suitable smaller number. The ratio of fluoride to phosphate (or other anion) may be, in some embodiments, at most 30:1. In some embodiments, the ratio of fluoride to phosphate may be at most 20:1, and may be, for instance, from 6:10 to 30:1 or from 6:10 to 2:1. The amount of phosphate may be increase relative to the amount of fluoride, and accordingly the $F:PO_4$ ratio can be less than 6:10; for instance, it can be 6:15, 6:20, 6:30, 6:40, or 6:50, or a suitable smaller number. In some embodiments of the invention, the ratio $F:Ca:PO_4$ is 6:10:1. In determining these ratios, it is contemplated that a margin of error of plus or minus about 3% may be taken into account. The invention is not deemed limited to the heretofore expressed ratios of fluoride to calcium and fluoride to phosphate; to the contrary, any suitable ratios may be employed. Similarly, the acid/anion is not limited to phosphoric acid/phosphate ion; to the contrary, other acids/anions may be deemed suitable.

The absolute amounts of fluoride, calcium, and phosphate in the composition may be any amounts suitable to allow for precipitation of calcium fluoride in a human oral cavity. Without limiting the generality of the foregoing, the fluoride component, expressed on a weight basis, in some embodiments may be at least 10 ppm, and in some embodiments may be at least 100 ppm, and in some embodiments ranges from 100 to 12000 ppm (12000 ppm=1.2%). Without limiting the generality of the foregoing, calcium can be present in some embodiments in an amount of at least 40 ppm, and in some embodiments at least 100 ppm, and in some embodiments 100-80,000 ppm (80,000 ppm=8%). In solution, the calcium ion concentration in some embodiments ranges up to 2M. Without limiting the generality of the foregoing, the phosphate or other anion in some embodiments can be present in an amount of at least 15 ppm, and in some embodiments at least 100 ppm, and in some embodiments 100-6000 ppm (6000 ppm=0.6%). These amounts are inclusive of free ions and other forms of the components may be varied depending on the nature of the composition and the intended use thereof.

For instance, the composition may take the form of dentifrice, a toothpaste, a gel, a lozenge, a rinse, or other dentally suitable composition. In these forms, the fluoride may be present in any suitable amounts. When in the form of, for instance, a rinse, the fluoride concentration may be at least 60 ppm, and in some embodiments at least 70 ppm, and in some embodiments at least 80 ppm, and in some embodiments at least 90 ppm, and in some embodiments at least 100 ppm. When in the form of a dentifrice or toothpaste, the fluoride may be present in amounts of at least 180 ppm, in some embodiments, at least 200 ppm, in some embodiments, at least 220 ppm, in some embodiments, at least 240 ppm, in some embodiments, at least 260 ppm, in some embodiments, at least 280 ppm, and in some embodiments, at least 300 ppm. When in the form of a fluoride delivery gel, the fluoride may be present in an amount of at least 1000 ppm, in some embodiments, at least 1100 ppm, in some embodiments, at least 1200 ppm, in some embodiments, at least 1300 ppm, in some embodiments, at least 1400 ppm, and in some embodiments, at least 1500 ppm. When in the form of a lozenge, the fluoride may be present in any suitable amount, such as 0.2 mo. Again, a margin of error of plus or minus 3% may be taken into account in determining the concentrations of these components, and again, these amounts are exemplary and are not limiting. These amounts may be lower than in typical conventional products intended for similar uses. For instance, typical rinses contain fluoride in amounts of 250 ppm (for over-the-counter products) and up to about 1000 ppm (for prescription products). Typical dentifrices and toothpastes contain fluoride in amounts of 500 ppm (for children's products) and of 1000-1500 ppm (for adult products), with higher limits for certain prescription products. Typical fluoride delivery gels contain 5000-6000 ppm fluoride and may contain up to 12,000 ppm fluoride. Typical lozenges contain 1 mg fluoride. In some embodiments, rinses, toothpastes, dentifrices, and gels may contain amounts of fluoride in these typical amounts and ranges.

Although it is not intended to limit the invention to a particular theory of operation, it is believed that the fluoride, calcium, and phosphate or glycerophosphate combine to form of a soluble complex of the three ions. It has been observed that, in many embodiments, the pH of a solution of fluoride, calcium, and phosphorous, when made in accordance with the present teachings, is lower than the theoretical pH expected of a composition that contains these materials in the indicated amounts. It is believed that this effect can be attributed to the formation of a complex of the various types of ions in the solution. The exact nature of the complex, if such a complex is indeed formed, has not been ascertained by the inventors.

As shown, for instance, in FIG. 1, the pH of a solution of sodium fluoride and phosphoric acid at a 6:1 ratio is relatively flat, increasing from a pH of about 4 with no fluoride to just under 5 at 600 mmol/L total fluoride concentration. Curves 2 and 3 represent respectively measured and calculated theoretical pH's of compositions that include sodium fluoride, calcium chloride, and phosphoric acid in a ratio of 6:10:1. As seen, again the calculated theoretical pH curve is relatively flat, ranging from just under 5 to a calculated low of about 3.5 with a minimum value reached at about 300 mmol/L fluoride. The actual pH, however, is significantly lower, falling below pH 1 at 600 mmol/L fluoride and not reaching a minimum near 300 mmol/L fluoride.

In some embodiments, the stability as against calcium fluoride precipitation of a composition that contains phosphate (or another anion) is improved relative to the stability of a similar composition containing calcium and fluoride in the absence of the phosphate or other anion. In Table 1, below, an analysis of various solutions included calcium and fluoride is reported. For each table entry, Solution B was added to Solution A to prepare a combined solution that included the indicated amounts of calcium and fluoride ions, and the stability of the solution over a period of a few minutes was observed. As seen, some, but not all, of the mixtures were somewhat stable over a short period of time as against calcium fluoride precipitation, such precipitation being indicated upon the development of cloudiness in the mixture.

TABLE 1

Fluoride/Calcium compositions with no phosphate

| No. | Solution A | Solution B | [F] mmol/L | [Ca] mmol/L | Appearance |
|---|---|---|---|---|---|
| 1 | CaCl$_2$ | NaF | 12 | 10 | Cloudiness develops very slowly |
| 2 | NaF | CaCl$_2$ | 12 | 10 | Cloudiness develops quickly |
| 3 | CaCl$_2$ | NaF | 24 | 20 | Cloudiness develops |
| 4 | NaF | CaCl$_2$ | 24 | 20 | Cloudiness develops |
| 5 | CaCl$_2$ | NaF | 96 | 50 | Clear |
| 6 | NaF | CaCl$_2$ | 96 | 50 | Slight cloudiness develops |
| 7 | CaCl$_2$ | NaF | 96 | 100 | Clear |
| 8 | NaF | CaCl$_2$ | 96 | 100 | Cloudiness develops |
| 9 | CaCl$_2$ | NaF | 96 | 200 | Clear |
| 10 | NaF | CaCl$_2$ | 96 | 200 | Slight cloudiness develops |
| 11 | CaCl$_2$ | NaF | 175 | 10 | Clear |
| 12 | NaF | CaCl$_2$ | 175 | 10 | Very slight cloudiness develops |
| 13 | CaCl$_2$ | NaF | 175 | 50 | Slight cloudiness develops very slowly |
| 14 | NaF | CaCl$_2$ | 175 | 50 | Cloudiness develops quickly |
| 15 | CaCl$_2$ | NaF | 175 | 100 | Clear; pH = 4.22 |
| 16 | NaF | CaCl$_2$ | 175 | 100 | Cloudiness develops immediately; pH = 4.56 |
| 17 | CaCl$_2$ | NaF | 175 | 200 | Clear |
| 18 | NaF | CaCl$_2$ | 175 | 200 | Slight cloudiness develops |
| 19 | CaCl$_2$ | NaF | 175 | 300 | Cloudiness develops slowly |
| 20 | NaF | CaCl$_2$ | 175 | 300 | Cloudiness develops |
| 21 | CaCl$_2$ | NaF | 175 | 400 | Clear; pH = 4.24 |
| 22 | NaF | CaCl$_2$ | 175 | 400 | Slight cloudiness develops; pH = 4.53 |
| 23 | CaCl$_2$ | NaF | 300 | 1000 | Cloudiness develops slowly |
| 24 | NaF | CaCl$_2$ | 300 | 1000 | Cloudiness develops immediately |
| 25 | CaCl$_2$ | NaF | 600 | 1000 | Cloudiness develops |
| 26 | NaF | CaCl$_2$ | 600 | 1000 | Cloudiness develops |

Measurements of free calcium and fluoride concentrations of those solutions that remained clear show that the free fluoride concentration was less than 10% of the total fluoride present in the solution. Likewise, free calcium was also significantly lower than the total amount of calcium in the solution.

These results suggest that a F/Ca complex formed, the complex removing the bulk of free F and Ca from solution. In addition, pH also decreased (compare, for instance, solution 15 v. 16). Nonetheless, this F/Ca complex is deemed metastable, because precipitation may occur over time or as a result of a temperature change, or when another electrolyte, such as sodium chloride or potassium chloride, is present. None of the foregoing compositions were stable for storage and transport.

In the following table, Table 2, analyses of various solutions of calcium, fluoride, and phosphoric acid are reported. These solutions (except no. 14) are supersaturated with respect to calcium fluoride, yet the solutions remained clear. All were tested for stability for storage and transport in accordance with the heretofore described methodology, and all were deemed stable for storage and transport (except for those compositions in which cloudiness was observed to develop). In preparing the solutions, the fluoride and phosphoric acid were first combined in a solution, and this combined solution then was mixed with a calcium-containing solution. As seen, cloudiness did not develop even when the concentration of fluoride was 1200 mmol/L. The stoichiometric ratio of the components was varied by decreasing the calcium and phosphate concentration separately; these results also are reported in Table 2.

TABLE 2

Fluoride/Calcium/Phosphate compositions

Combined Solution

| No. | [F] mmol/L | [Ca] mmol/L | [$H_3PO_4$] mmol/L | pH | Appearance |
|---|---|---|---|---|---|
| All solutions with [F]:[Ca]:[$H_3PO_4$] = 6:10:1 stable compositions | | | | | |
| 1 | 1200 | 2000 | 200 | 0.32 | Clear |
| 2 | 600 | 1000 | 100 | 0.89 | Clear |
| 3 | 300 | 500 | 50 | 1.35 | Clear |
| 4 | 150 | 250 | 25 | 1.70 | Clear |
| 5 | 96 | 160 | 16 | 1.90 | Clear |
| 6 | 48 | 80 | 8 | 2.21 | Clear |
| 7 | 24 | 40 | 4 | 2.48 | Clear |
| 8 | 12 | 20 | 2 | 2.77 | Clear |
| 8a | 12 | 200 | 2 | 2.43 | Clear |
| 8b | 12 | 20 | 20 | 2.19 | Clear |
| 9 | 6 | 10 | 1 | 3.06 | Clear |
| 10 | 3 | 5 | 0.5 | 3.35 | Clear |
| 11 | 1.5 | 2.5 | 0.25 | 3.67 | Clear |
| 12 | 1 | 1.67 | 0.167 | 3.81 | Clear |
| 13 | 0.5 | 0.83 | 0.083 | 4.08 | Clear |
| 14 | 0.25 | 0.42 | 0.042 | 4.35 | Clear |
| Effect of [Ca] on stability | | | | | |
| 15 | 600 | 1000 | 100 | 0.79 | Clear |
| 16 | 600 | 500 | 100 | 1.08 | Clear |
| 16a | 600 | 400 | 100 | 1.26 | Clear |
| 16b | 600 | 300 | 100 | 1.83 | Clear |
| 16c | 600 | 200 | 100 | 4.01 | Cloudiness develops |
| 17 | 600 | 100 | 100 | 4.49 | Cloudiness develops |
| 18 | 600 | 50 | 100 | 4.69 | Cloudiness develops |
| 19 | 600 | 10 | 100 | 4.85 | Cloudiness develops |
| Effect of [$H_3PO_4$] on stability | | | | | |
| 20 | 600 | 1000 | 1000 | 0.51 | Clear |
| 21 | 600 | 1000 | 500 | 0.62 | Clear |
| 22 | 600 | 1000 | 100 | 0.88 | Clear |
| 23 | 600 | 1000 | 30 | 1.16 | Clear |
| 23a | 600 | 1000 | 20 | 1.17 | Clear |
| 24 | 600 | 1000 | 10 | 1.45 | Cloudiness develops |

Figure 2:
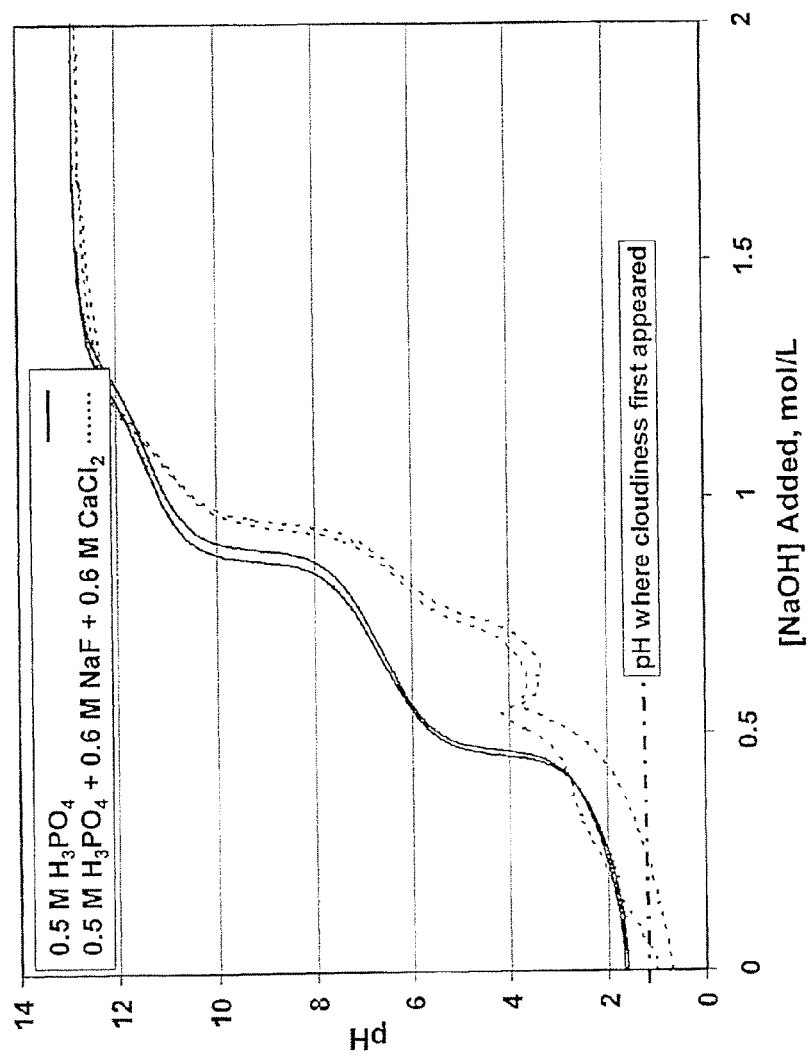
FIG. 2 is a graph that illustrates the pH of aqueous compositions that contain calcium, fluoride, and phosphate as a function of added sodium hydroxide, the phosphate being present at a concentration of 0.5 M.

As shown in FIG. 2, sodium hydroxide was added to various compositions, the compositions including phosphoric acid alone or phosphoric acid in combination with sodium fluoride and calcium fluoride. As expected, the pH of a phosphoric acid solution to which sodium hydroxide was added increased generally as the amount of added sodium hydroxide increased, with certain flat areas of the curve representing the buffering capability of phosphoric acid. The pH of the representative inventive composition, however, did not increase in the same manner, and indeed the pH decreased with sodium hydroxide addition at a sodium hydroxide concentration of about 0.6 M. It was observed that addition of sodium hydroxide caused a large amount of $CaF_2$ precipitation at a pH of about 1.7. Again, while the invention is not attended to be limited to a particular theory of operation, it is believed that an increase of pH destabilized the F—Ca—$PO_4$ complex and induced $CaF_2$ precipitation.

Figure 3:
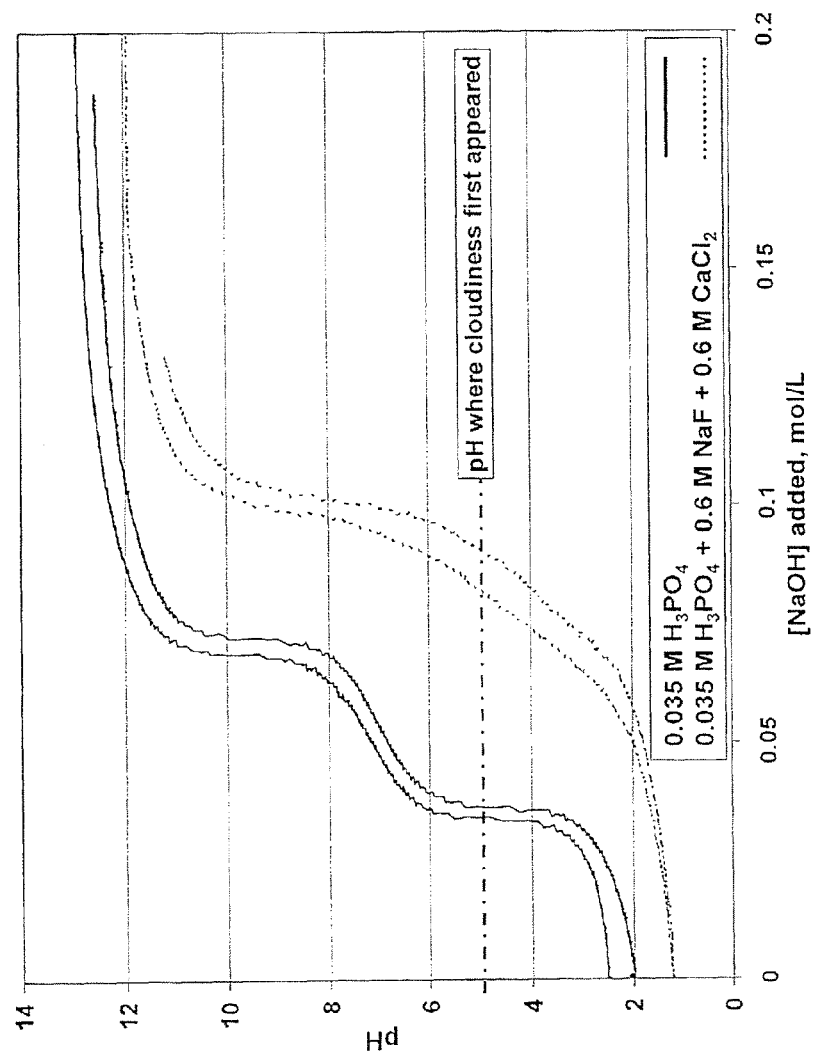
FIG. 3 is a graph that illustrates the pH of aqueous compositions that contain calcium, fluoride, and phosphate as a function of added sodium hydroxide, the phosphate being present at a concentration of 0.03 M.

FIG. 3 shows similar data to that of FIG. 2, except that the amount of phosphoric acid was decreased. With the lower phosphoric acid concentration, a much smaller amount of sodium hydroxide addition was needed to raise the pH. Calcium fluoride precipitation first occurred at a higher pH of about 4.8. The decrease in pH observed with respect to FIG. 2 was not observed at the lower concentration of phosphoric acid.

Solutions of glycerophosphate, fluoride, and calcium were evaluated, as per the compositions given in the following Table 3.

TABLE 3

Fluoride-Calcium-Glycerophosphoric Acid ($GPO_4$) compositions

Combined Solution

| No. | [F] mmol/L | [Ca] mmol/L | [$GPO_4$] mmol/L | pH | Appearance |
|---|---|---|---|---|---|
| All solutions with [F]:[Ca]:[glycerophosphoric acid] = 6:10:1 | | | | | |
| 1 | 600 | 1000 | 100 | 0.80 | Clear* |
| 2 | 120 | 200 | 20 | 1.69 | Clear |
| 3 | 60 | 100 | 10 | 2.02 | Clear |
| 4 | 12 | 20 | 2 | 2.77 | Clear |
| 5 | 6 | 10 | 1 | 3.06 | Clear |

All of the compositions except for composition 1 were stable for storage and transport, as determined by holding the solutions at 7° C. for three days Again, without limiting the invention to a particular theory of operation, it is believed that glycerophosplhate formed a soluble complex with calcium and fluoride.

Solutions of phosphonoacetate, fluoride, and calcium were evaluated, as per the compositions given in the following Table 4.

TABLE 4

Fluoride-Calcium-Phosphonoacetic Acid compositions

Combined Solution

| No. | [F] mmol/L | [Ca] mmol/L | [C₂H₅O₅P] mmol/L | pH | Appearance (after 10 minutes) |
|---|---|---|---|---|---|
| All solutions with [F]:[Ca]:[phosphonoacetic acid] = 6:10:1 | | | | | |
| 1 | 600 | 1000 | 100 | 0.65 | Clear |
| 2 | 120 | 200 | 20 | 1.59 | Clear |
| 3 | 60 | 100 | 10 | 1.88 | Clear |
| 4 | 12 | 20 | 2 | 2.59 | Clear |
| 5 | 6 | 10 | 1 | 2.90 | Clear |

Composition 5 was stable when held for 70° C. for one day. The remaining compositions were not stable when held for 70° C. for one day. It is contemplated that better stability for storage and transport might be realized if a different ratio of fluoride to calcium to anion were selected.

In use, the heretofore described compositions may be used in any dentally suitable application. Generally, the compositions are provided and applied to a human oral cavity in an amount effective to cause precipitation of calcium fluoride onto one or more oral surfaces, such as tooth surfaces. The composition may be self applied by a patient (especially in a case of a toothpaste or rinse), or, in some embodiments, the composition may be applied by a person other than the patient. "Patient" does not necessarily connote a person under medical or dental care, but in some embodiments the patient may be a person who is under medical or dental care. For instance, certain dentifrice compositions may be available only by prescription, and applied by dentist or dental assistants.

The pH of the compositions should be a pH that is dentally acceptable. In many embodiments, the pH is less than about 5. In some embodiments, particularly where the pH is less than about 2, the surfaces of the mouth to which the composition is to be applied may be "pre-painted" with a basic composition, to guard against damage to the oral cavity from excess acidity.

The compositions are useful in connection with general prophylaxis, in connection with specific fluoride "booster" treatments, or otherwise generally in methods for providing dental fluoride to a patient. In some embodiments, in connection with the obturation of dental tubules. In some such embodiments, the composition may be useful in connection with desensitization treatment, whereby, by obturating dental tubules, tooth sensitivity is decreased. In accordance with such embodiments, the composition may be applied to a dentin surface in an amount affected to cause calcium fluoride to precipitate in dental tubules. In accordance with any of the foregoing embodiments, the composition may be applied over any suitable period of time. In some cases, the period of time ranges from 0.5 minutes to 2 hours; in some embodiments the period of time ranges from 0.5 to 4 minutes.

The composition may be applied in a single-composition treatment, but need not be so applied. For instance, in other embodiments, other compositions, such as the heretofore described basic "pre-paint," a surfactant, gelling agent or detergent, or other suitable ingredient, may be provided in addition to the composition of the invention, either before or after application of the inventive composition.

The following non-limiting Examples are provided to illustrate the invention.

EXAMPLE 1

In Vitro Analysis

The ability of the F—Ca—P mixtures to deposit fluoride into oral substrates was evaluated in vitro with the use of filter discs as the model substrates, as described in Takagi S. et al., "Effect of a Low-Fluoride-Content, Two-Component Rinse on Fluoride Uptake and on De- and Remineralization of Enamel Lesions: An In Vitro Study," *Caries Res.* 35:223-228 (2001). Hydrophilic membrane filter discs with an averaged pore size of 0.2 μm and a relatively constant thickness (150 μm) and pore volume (75%) were provided. For each of the mixtures specified in the following Table, the discs were immersed in the mixture for 1 minute and rinsed for 20 seconds with a CaF₂ saturated solution to remove F that was not firmly attached to the disc. Each disc was then immersed in a 0.5 M HClO₄ etchant solution for 30 minutes to dissolve the deposited F. The etchant then was neutralized and analyzed for F.

As shown in Table 5, for a given F content, the F deposition by the F—Ca—P mixture was much higher than that produced by a solution that contained only F.

TABLE 5

Fluoride deposition.

| Treatment solution | F deposition, μg/cm² | % improvement by F—Ca—P |
|---|---|---|
| 12 mM NaF (228 ppm) | 0.74 ± 0.06 | 691% |
| 12 mM NaF + 20 mM CaCl₂ + 2 mM H₃PO₄ | 5.10 ± 0.50 | |
| 12 mM NaF + 20 mM CaCl₂ + 2 mM H₃PO₄ in 30% H₂O₂ | 5.27 ± 0.09 | 712% |
| 12 mM NaF + 20 mM CaCl₂ + 1 mM KH₂PO₄ | 5.30 ± 0.10 | 716% |
| 12 mM NaF + 200 mM CaCl₂ + 20 mM H₃PO₄ | 7.92 ± 0.18 | 1070% |
| 12 mM NaF + 200 mM CaCl₂ + 0.7 mM H₃PO₄ | 8.31 ± 0.31 | 1123% |
| 12 mM NaF + 20 mM CaCl₂ + 20 mM H₃PO₄ | 7.83 ± 0.28 | 1058% |
| 12 mM NaF + 20 mM CaCl₂ + 0.7 mM H₃PO₄ | 8.15 ± 0.37 | 1101% |
| 12 mM NaF + 7 mM CaCl₂ + 0.7 mM H₃PO₄ | 7.01 ± 0.31 | 947% |
| 87.7 mM NaF (1667 ppm F) | 2.24 ± 0.39 | 744% |
| 87.7 mM NaF + 146.2 mM CaCl₂ + 14.6 mM H₃PO₄ | 16.7 ± 1.20 | |
| 87.7 mM NaF + 146.2 mM CaCl₂ + 14.6 mM H₃PO₄ in 30% H₂O₂ | 18.1 ± 0.49 | 835% |
| 87.7 mM NaF + 146.2 mM CaCl₂ + 14.6 mM H₃PO₄ (22 days at 50° C.) | 17.3 ± 0.10 | 772% |

Values are mean ± s.d. (n = 3)

EXAMPLE 2

In Vivo Salivary Fluoride Analysis

Two human subjects refrained from eating or drinking for 2 hours. Each subject then rinsed for 1 minute with a slurry prepared by mixing 5 grams of a commercial 5000 ppm F dentifrice (NaF as source of F) or the experimental 5000 ppm F (F—Ca—P mixture as source of F) dentifrice with 15 grams of distilled water. The [F]:[Ca]:[P] molar ratio in the dentifrice of the invention was 6:10:1. After spitting out the dentifrice slurry the subject rinsed for 10 seconds with 20 mL of distilled water. The subjects continued to refrain from food and drink for 1 hour after dentifrice application, whereupon approximately 2 mL of saliva was collected. One mL of each saliva sample was added to 1 mL of 0.5 M perchloric acid and allowed to stand for about 5 minutes. Two mL of TISAB (Total Ionic Strength Adjustment Buffer) that also contained 0.25 M NaOH was then added, and the sample was analyzed for F content. As shown in Table 6, a much higher 1-hour salivary F was produced by the dentifrice of the invention. The experiment was repeated with the same two subjects.

TABLE 6

Fluoride deposition with dentifrice.

| Test Product | Salivary F concentration, mM | % improvement by F—Ca—P |
|---|---|---|
| Commercial F dentifrice (5000 ppm F) | 0.151 ± 0.061 | 2310% |
| F—Ca—P dentifrice (5000 ppm F) | 3.49 ± 2.66 | |

Values are mean ± s.d. (n = 2)

EXAMPLE 3

Second In Vivo Salivary Fluoride Analysis

Two subjects refrained from eating or drinking for 2 hours. Each subject then rinsed for 1 minute with 20 mL of a 228 ppm F NaF rinse or a 228 ppm F F—Ca—P rinse having a [F]:[Ca]:[P] molar ratio of 6:10:1. No water rinse was given after the F rinse. No food or drink was allowed following the treatment until approximately 2 mL of saliva was collected at 1 hour after the rinse application. One mL of saliva sample was added to 1 mL of 0.5 M perchloric acid and allowed to stand for about 5 minutes. Two mL of TISAB that also contained 0.25 M NaOH was then added and the sample was analyzed for F content. The results given in Table 7 showed a greatly increased 1-hour salivary F for the F—Ca—P treated subject.

TABLE 7

Fluoride deposition with mouth rinse.

| Test Product | Salivary F concentration, mM | % improvement by F—Ca—P |
|---|---|---|
| NaF rinse (228 ppm F) | 0.081 ± 0.021 | 2901% |
| F—Ca—P rinse (228 ppm F) | 2.35 ± 0.76 | |

Values are mean ± s.d. (n = 2)

EXAMPLE 4

In Vitro Dentin Desensitization Analysis

This study evaluated the effectiveness of a concentrated F—Ca—P solution for dentin desensitization treatment.

Dentin slabs were etched with 6% citric acid to produce a clean surface with completely open dentin tubules. The specimens were then treated with an alkaline solution (5N KOH) using a cotton swab for 30 sec, and dried by a gentle stream of compressed air. A F—Ca—P mixture (0.6 M NaF, 1.38 M $H_3PO_4$, 2 M $CaCl_2$) was then applied for 4 min, and the specimen surfaces were similarly air dried. It is believed that residual KOH caused precipitation of $CaF_2$ from the F—Ca—P mixture.

Dentin permeability was measured before and after the treatment using an in vitro dentin permeability model, as described in Cherng et al., "Reduction in Dentin Permeability Using a Slurry Containing Dicalcium Phosphate and Calcium Hydroxide," *J. Biomed. Mater. Red Part B: Appl. Biomater.* 78B:291-295 (2006).

Figure 4:
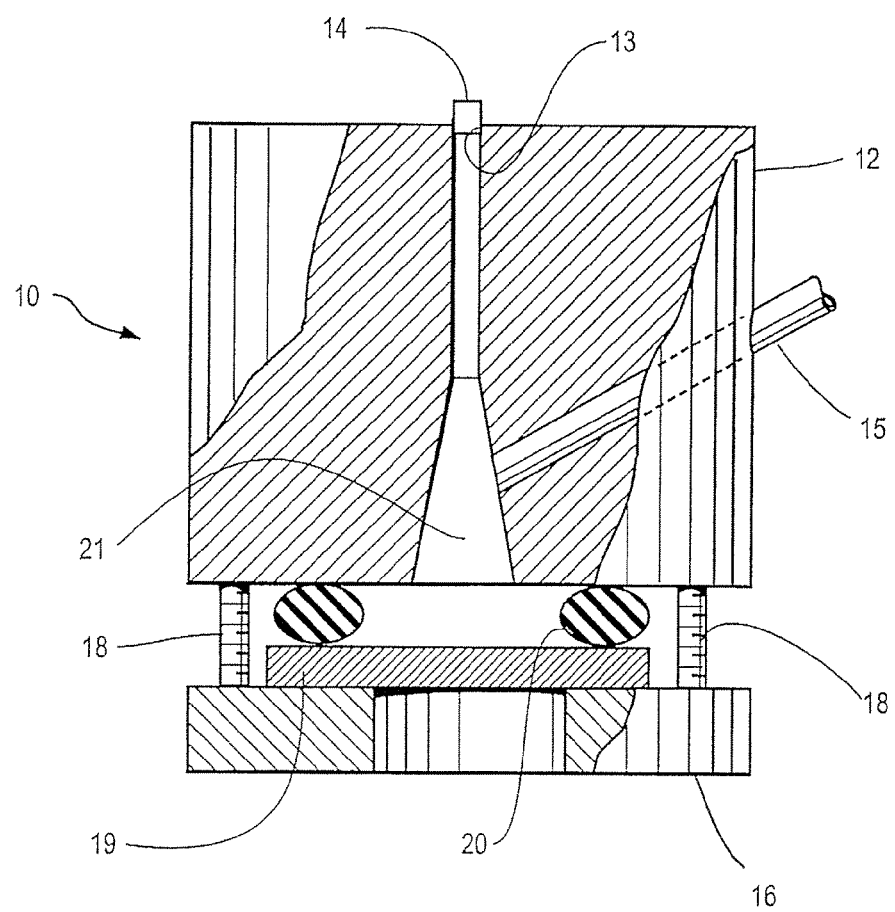
FIG. 4 is an elevational view, partially cut away, illustrating a flow cell used for measuring dentin permeability in connection with Example 4.

As shown in FIG. 4, the device 10 for measuring dentin permeability included a housing 12 having a vent hole 13, which is equipped with a removable plug 14, and a side flow channel 15 that was connected to a flow rate measuring device and to a source (not shown) of PBS (phosphate buffered saline). In the illustrated embodiment, the housing was made of a reinforced glass fiber matrix. The housing was connected to a disc 16 made of similar material via a pair of positioning screws 18, and this assembly was held together by a clamp (not shown). In evaluating dentin samples, each dentin sample 19 was cemented onto the disk 16 and the screws 18 fastened into place. The sample 19 was separated from the housing 12 via O-ring 20. Once the dentin sample was positioned as shown, the plug 14 was removed the PBS was introduced via gravity through the side flow channel 15, until the cavity 21 filled with liquid. At that point, the plug 14 was positioned over the vent hole 13, and PBS was allowed to flow through the dentin sample. The flow rate through each dentin sample was determined before and after treatment.

A 97% reduction in dentin permeability was produced. After rigorous brushing, the permeability increased slightly, but still exhibited a 48% reduction. This shows that the treatment was highly effective in obturation of open dentin tubules, and that the product of treatment was resistant to mechanical abrasion.

The specimens, post-brushing, were then placed in a saliva-like solution (SLS) for 5 days simulating exposure of treated specimens to oral conditions. The permeability was found to further decrease, exhibiting an 87% reduction even after brushing. This observation suggests that fluoride that precipitated from the inventive F—Ca—P mixture induced significant additional mineral precipitation from the SLS, thereby leading to further obturation of dentin tubules and leading to an increase in mechanical abrasion. From these results, it is believed that certain F—Ca—P formulations are effective for dentin desensitization treatments.

It is thus seen that, in certain embodiments, the invention provides composition, kits, and methods. The invention can provide a composition that is stable for storage and transport and that allows large amounts of calcium fluoride precipitation than possible via certain prior art compositions.

All references, including publications, patent applications, and patents, cited herein are hereby incorporated by reference. In any listing of possible ingredients or components, mixtures of the possible ingredients or components are contemplated unless expressly indicated otherwise. The description of certain embodiments as "preferred" or exemplary embodiments, and other recitation of embodiments, features, or ranges as being preferred or exemplary, is not deemed to be limiting, and the invention is deemed to encompass embodiments that are presently deemed to be less preferred and that are not exemplified. All methods described herein can be performed in any suitable order unless otherwise indicated herein or otherwise clearly contradicted by context. The use of any and all examples, or exemplary language (e.g., "such as") provided herein, is intended to illuminate the invention and does not pose a limitation on the scope of the invention unless otherwise claimed. Any statement herein as to the nature or benefits of the invention or of the preferred embodiments is not intended to be limiting, and the appended claims should not be deemed to be limited by such statements. More generally, no language in the specification should be construed as indicating any non-claimed element as being essential to the practice of the invention. This invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. The description herein of any reference or patent, even if identified as "prior,", is not intended to constitute a concession that such reference or patent is available as prior art against the present invention.

The invention claimed is:

1. A dental composition comprising calcium, at least 100 ppm of fluoride, and a stabilizing anion of phosphate glycerophosphate, or phosphonoacetate, the molar ratio of fluoride to calcium being at most 2:1 and the molar ratio of fluoride to the stabilizing anion being at most 30:1, said composition (i) being sufficiently stable to inhibit precipitation of calcium fluoride during an aging test comprising storage at 50° C. in a sealed container for 1 week, (ii) being sufficiently unstable in a human oral cavity to cause precipitation of calcium fluoride, and (iii) not being sufficiently stable to inhibit precipitation of calcium fluoride during said aging test in the absence of said stabilizing anion.

2. A composition according to claim 1, said composition is a dentifrice.

3. A composition according to claim 1, said composition is a toothpaste.

4. A composition according to claim 1, said composition is a gel.

5. A composition according to claim 1, said composition is a lozenge.

6. A composition according to claim 1, said composition is a rinse.

7. A composition according to claim 1, the molar ratio of fluoride to calcium ranging from 6:10 to 6:5.

8. A composition according to claim 7, the molar ratio of fluoride to stabilizing anion ranging from 6:10 to 20:1.

9. A composition according to claim 1, the molar ratio of fluoride to stabilizing anion ranging from 6:10 to 20:1.

10. A composition according to claim 1, the molar ratio of F:Ca:PO$_4$ being 6:10:1.

11. A composition according to claim 1, including F in an amount of at least 1000 ppm.

12. A composition according to claim 1, said composition taking the form of a rinse.

13. A composition according to claim 1, said composition comprising a dentifrice, said composition comprising F in an amount of at least 180 ppm.

14. A composition according to claim 1, said composition being an aqueous composition having a pH of 5 or less.

15. A kit comprising a sealed container containing an amount of the composition of claim 1 effective for dental application to at least one human.

16. A composition comprising calcium, a stabilizing anion of phosphate, glycerophosphate, or phosphonoacetate, and at least 100 ppm of fluoride, said composition being in a form of a rinse and (i) being sufficiently stable to inhibit precipitation of calcium fluoride during an aging test comprising storage at 50° C. in a sealed container for 1 week, (ii) being sufficiently unstable in a human oral cavity to cause precipitation of calcium fluoride, and (iii) not being sufficiently stable to inhibit precipitation of calcium fluoride during said aging test in the absence of said stabilizing anion.

17. A composition comprising calcium, phosphate and fluoride, said composition being in a form of a dentifrice containing at least 180 ppm fluoride, said composition (i) being sufficiently stable to inhibit precipitation of calcium fluoride during an aging test comprising storage at 50° C. in a sealed container for 1 week, (ii) being sufficiently unstable in a human oral cavity to cause precipitation of calcium fluoride and (iii) not being sufficiently stable to inhibit precipitation of calcium fluoride during said aging test in the absence of said stabilizing anion.

18. A method for providing dental fluoride to a patient, the method comprising:
applying to the oral cavity of a patient at least an amount of the dental composition of claim 1 sufficient to cause calcium fluoride to precipitate from said composition.

19. A method according to claim 18, comprising applying to a tooth surface of said patient an amount of an aqueous composition having a pH that is higher than the pH of said dental composition.

20. A method according to claim 18, said dental composition being self-applied to said oral cavity by said patient.

21. A method according to claim 18, said dental composition being applied to said oral cavity by a person other than said patient.

22. A method according to claim 18, the molar ratio of fluoride to calcium being at most 6:5 and the molar ratio of fluoride to phosphate being at most 20:1.

23. A method according to claim 18, said composition is a dentifrice.

24. A method according to claim 18, said composition is a toothpaste.

25. A method according to claim 18, said composition is a gel.

26. A method according to claim 18, said composition is a lozenge.

27. A method according to claim 18, said composition is a rinse.

28. A method according to claim 18, said anion is phosphate.

29. A method according to claim 18, said anion is glycerophosphate.

30. A dental composition consisting essentially of a biocompatible mixture of calcium, at least 100 ppm of fluoride, and a stabilizing anion of phosphate, glycerophosphate, or phosphonoacetate, said composition (i) being sufficiently stable to inhibit precipitation of calcium fluoride during an aging test comprising storage at 50° C. in a sealed container for 1 week, (ii) being sufficiently unstable in a human oral cavity to cause precipitation of calcium fluoride, and (iii) not being sufficiently stable to inhibit precipitation of calcium fluoride during said aging test in the absence of said stabilizing anion.

31. A composition according to claim 30, said composition is a dentifrice.

32. A composition according to claim 30, said composition is a toothpaste.

33. A composition according to claim 30, said composition is a gel.

34. A composition according to claim 30, said composition is a lozenge.

35. A composition according to claim 30, said composition is a rinse.

36. A composition according to claim 30, said anion is phosphate.

37. A composition according to claim 30, said anion is glycerophosphate.

38. A method for obturating dentin tubules in a patient in need of dental tubule obturation, comprising:
administering to said patient at least an amount of the dental composition of claim 1 sufficient to cause calcium fluoride to precipitate in dental tubules of said patient.

39. A method according to claim 38, said anion is phosphate.

40. A method according to claim 38, said anion is glycerophosphate.

41. A dental composition comprising calcium, at least 100 ppm of fluoride, and a stabilizing anion of phosphate, glycerophosphate, or phosphonoacetate, said composition being sufficiently stable to inhibit precipitation of calcium fluoride during an aging test comprising storage at 50° C. in a sealed container for 1 week, (ii) being sufficiently unstable in a human oral cavity to cause precipitation of calcium fluoride, and (iii) not being sufficiently stable to inhibit precipitation of calcium fluoride during said aging test in the absence of said stabilizing anion, wherein said composition comprises an aqueous composition having a pH of 5 or less.

42. The composition as set forth in claim 41 wherein said stabilizing anion is an anion of phosphoric acid.

43. The composition of claim 42 further including sodium hydroxide.

44. The composition of claim 42 wherein said phosphoric acid releases phosphate ions maintained in solution.

45. The composition of claim 44 wherein the molar ratio of fluoride to calcium being at most 2:1 and the molar ratio of fluoride to phosphate being at most 30:1.

\* \* \* \* \*

UNITED STATES PATENT AND TRADEMARK OFFICE
CERTIFICATE OF CORRECTION

| | | |
|---|---|---|
| PATENT NO. | : 8,956,594 B2 | Page 1 of 1 |
| APPLICATION NO. | : 11/552414 | |
| DATED | : February 17, 2015 | |
| INVENTOR(S) | : Laurence C. Chow et al. | |

It is certified that error appears in the above-identified patent and that said Letters Patent is hereby corrected as shown below:

In the Specification

Column 1, Lines 13-20, should read:
STATEMENT OF FEDERALLY SPONSORED RESEARCH
This invention was made with government support under grant DE005129 awarded by the National Institutes of Health. The government has certain rights in the invention.

Signed and Sealed this
Thirtieth Day of November, 2021

Drew Hirshfeld
*Performing the Functions and Duties of the*
*Under Secretary of Commerce for Intellectual Property and*
*Director of the United States Patent and Trademark Office*